US 6,592,567 B1

(12) United States Patent
Levin et al.

(10) Patent No.: US 6,592,567 B1
(45) Date of Patent: *Jul. 15, 2003

(54) KIDNEY PERFUSION CATHETER (75) Inventors: Howard R. Levin, Teaneck, NJ (US); Mark Gelfand, New York, NY (US); Steve Bernard, Yonkers, NY (US)

(73) Assignee: CHF Solutions, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/454,605

(22) Filed: Dec. 7, 1999

(51) Int. Cl.⁷ .................... A61M 31/00; A61M 29/00
(52) U.S. Cl. ........................... 604/509; 604/101.01
(58) Field of Search .................. 604/28, 4.01, 6.11, 604/8, 9, 27, 30, 40, 506, 508, 509, 99.01, 101.03, 510, 67, 95.03, 103.05, 123, 97.03, 98.02, 500, 919, 507

(56) References Cited

U.S. PATENT DOCUMENTS

| 3,882,862 A | | 5/1975 | Berend |
| 4,379,452 A | | 4/1983 | DeVries |
| 4,464,164 A | | 8/1984 | Troutner et al. |
| 4,562,597 A | | 1/1986 | Possis et al. |
| 4,577,631 A | * | 3/1986 | Kreamer .................. 604/907 |
| 4,813,930 A | * | 3/1989 | Elliott .................... 600/585 |
| 4,883,459 A | * | 11/1989 | Calderon .................. 600/4 |
| 5,158,540 A | * | 10/1992 | Wijay et al. ........... 604/101.05 |
| 5,167,628 A | | 12/1992 | Boyles |
| 5,290,227 A | | 3/1994 | Pasque |
| 5,308,319 A | | 5/1994 | Ide et al. |
| 5,326,374 A | | 7/1994 | Ilbawi et al. |
| 5,332,403 A | | 7/1994 | Kolff |
| 5,399,352 A | | 3/1995 | Hanson |
| 5,505,701 A | | 4/1996 | Anaya Fernandez de Lomana |
| 3,655,548 A | | 8/1997 | Nelson et al. |
| 3,695,457 A | | 12/1997 | Goar et al. |
| 5,755,779 A | | 5/1998 | Horiguchi |
| 5,776,109 A | | 7/1998 | Jarvik |
| 5,824,071 A | | 10/1998 | Nelson et al. |
| 6,086,527 A | | 7/2000 | Talpade |
| 6,086,553 A | | 7/2000 | Akbik |
| 6,200,260 B1 | | 3/2001 | Bolling |
| 6,322,548 B1 | * | 11/2001 | Payne et al. ............... 604/500 |
| 2001/0014799 A1 | * | 8/2001 | Schwartz ................. 604/508 |

FOREIGN PATENT DOCUMENTS

DE 3406294 A1 9/1985

* cited by examiner

Primary Examiner—Brian L. Casler
Assistant Examiner—Matthew DeSanto
(74) Attorney, Agent, or Firm—Nixon & Vanderhye P.C.

(57) ABSTRACT

A kidney perfusion catheter assembly is disclosed having an introducer catheter, a renal artery seal, a perfusion tip, and a guide wire. The perfusion catheter provides a flow of supplemental blood to increase the local blood pressure in the renal artery and to perfuse the kidney. The introducer catheter is maneuvered through the femoral artery to the aorta and positioned at the branch of a renal artery. The perfusion catheter tip is telescoped from the distal end of the introducer catheter into the renal artery. A blood pump attached to the proximal end of the perfusion catheter assembly provides a flow of blood that streams from the perfusion catheter tip into the renal artery. This stream of blood increases the pressure and volume of the blood flowing through the renal artery. The catheter includes a seal to block the opening of the renal artery to prevent the runoff of the blood from the renal artery into the aorta. The catheter also includes a brace to secure the perfusion catheter tip in the aorta without distending the renal artery.

11 Claims, 9 Drawing Sheets

KIDNEY PERFUSION CATHETER

FIELD OF THE INVENTION

This invention generally relates to in-situ perfusion of an organ in a human or animal. In particular, the invention relates to a perfusion catheter for providing supplemental blood flow to a kidney.

BACKGROUND OF THE INVENTION

A long-felt need exists for a renal therapy device that perfuses kidney(s) with blood or another perfusion substance for extended periods, such as for days. Kidneys filter blood to remove body fluids, sodium and toxins, which are expelled from the body as urine. The filtration of blood is performed by a specialized network of capillaries in the kidneys. To properly pass through the kidneys, the blood pressure at the renal artery (the inlet to the kidneys) should be sufficient to force the blood through the network of capillaries.

Kidneys function best when the blood pressure is within a range of normal mean blood pressures, e.g., 60 to 120 mm Hg. When the blood pressure in the renal artery falls below this range of normal pressure, blood does not pass through the kidneys in sufficient volume to properly filter all of the blood in a circulatory system of a patient. Under low blood pressure conditions, the kidneys suffer from impaired renal perfusion which results in a decrease in urine output (and hence a corresponding build-up of fluids, sodium and toxins in the body), unfavorable change of neurohormonal stimulation and increased vasoconstriction (contraction of blood vessels). Prolonged impaired renal perfusion can lead to acute tubular necrosis, renal failure and ultimately dependency on artificial kidney for life.

Impaired renal perfusion may result from chronic heart failure. Chronic heart failure is a condition in which the heart typically deteriorates over an extended period of time, e.g., months or years. Heart failure is a clinical syndrome or condition characterized by (1) signs and symptoms of intravascular and interstitial volume overload, including shortness of breath, fluid in lungs, and edema, and (2) manifestations of inadequate tissue perfusion, such as fatigue or poor exercise tolerance. These signs and symptoms result when the heart is unable to generate a cardiac output sufficient to meet the body's demands. Heart failure is a major public health problem. The National Heart, Lung, and Blood Institute has estimated that more than 5 million Americans have heart failure and that about 400,000 new cases of heart failure are diagnosed each year. Total treatment costs for heart failure-including physician visits, drugs, and nursing home stays—were more than $10 billion in 1990.

A failing heart may not be able to generate sufficient blood pressure to properly perfuse the kidneys. A healthy heart pumps blood by increasing the kinetic energy (pressure and/or velocity) of the blood flowing through a person's circulatory system. The energy imparted by a heart to the blood flow is normally sufficient to cause the blood to circulate through the lungs, kidney and other organs of a human body. A failing heart is generally unable to maintain normal blood pressure within the circulatory system of a person. Blood pressure tends to progressively decrease as the heart. progressively fails in a patient suffering from chronic heart failure. Accordingly, chronic heart failure can lead to chronic impaired renal perfusion. Chronic heart failure patients are frequently admitted to the hospital with an onset of acute heart failure, which is an abrupt worsening of their condition that requires intensive care. During these periods of acute hypotension (or low blood pressure) their kidneys are particularly at risk from hypotension and can be severely injured.

There is a long-felt (although unrecognized) need for devices that can treat chronic impaired renal perfusion and, specifically, treat this condition in connection with the acute and chronic heart failure. In this condition patients blood pressure falls below the minimum level required for kidney function. As a result patients are admitted to the hospital with fluid overload resulting from the retention of fluid and sodium by the kidneys. To treat fluid overload, a device is needed that increases the arterial blood pressure at the kidney for extended periods, such as for several days.

In clinical practice it is sometimes desirable to isolate and perfuse an organ, such as the kidney, brain or liver. An organ suffering from inadequate blood flow, e.g., low systemic arterial pressure, may result in ischemia, organ shutdown or stroke. Extracorporeal perfusion of an organ is the process of artificially providing supplemental blood to that organ from an external source, usually a blood pump. The supplemental blood flow to the organ enables the organ to continue function properly, to avoid distressing the organ and may protect or revive an organ suffering from inadequate blood flow.

During perfusion, the blood or blood substitute is supplied to the organ by extracorporeal circuits from an external source, or may be blood drawn from the body and pumped by back into the body at the organ. An extracorporeal circuit, such as a blood pump connected by tubes and catheters to the body, may provide the blood to the organ for perfusion. The blood pump increases the kinetic energy of the blood or the perfusate, increases the perfusion pressure gradient, and sometimes, an oxygenator to add oxygen to the blood stream.

A kidney perfusion catheter is a device that increases the blood pressure at the kidney, and specifically in the renal artery. A catheter is typically a long, thin tube inserted through a patient's skin and into an artery or a vein. The catheter is connected at one end (commonly referred to as its proximate end) to a blood or saline bag, a blood pump or other medical device external to the body. Many people have had short catheters inserted into a vein in their arm to draw blood for blood donations, dialysis, or to receive blood during hospitalization.

Longer catheters exist that are inserted through the skin at the groin into the femoral artery (or vein). These longer catheters are advanced by an interventional radiologist or cardiologist through the artery to a body organ, such as the heart or kidney. These longer catheters often include guide wires, lumens, balloons, and other devices that perform a variety of catheter functions within an artery or organ. For example, a guide wire typically assists the physician in maneuvering the tip of the catheter along the passages of an artery to the intended position in the artery or organ. Once the catheter is properly positioned within a blood vessel, an instrument can be advanced via an internal lumen of the catheter to perform a therapeutic clinical intervention such as an ablation or dilatation or a diagnostic intervention such as angiography. Lumens are typically tubular passages within the catheter for the guide wires, sensor wires, and to pass blood or other fluids through the catheter.

Catheters exist for short-term perfusion of organs during cardiac surgery and other operations. Surgeons also are known to temporarily perfuse selected organs with extracorporeal pumps when major blood vessels, such as the aorta, are being repaired during surgery, vascular intervention and medical treatment. In addition, kidney perfusion catheters have been disclosed that perfuse kidneys in a dead patient until the kidneys are harvested for transplant. These catheters are not suitable for use beyond a few minutes or hours, and would be injurious to the patient if used for several days.

Existing catheters for in-situ perfusion of isolated organs or parts of the body with blood or chemical include a catheter for pelvic perfusion that isolates a portion of a major artery with two occluding balloons. The balloons are attached to a catheter to form a dumb-bell shape in which the balloons are at opposite ends of a tubular catheter section. The balloons anchor the catheter in an artery, form dams blocking the artery and allow the catheter to increase the blood pressure in the arterial section between the balloons. Fluid is infused by the catheter into the space between two balloons to perfuse organs that are connected to arterial branches stemming the isolated segment of the artery between the balloons.

The dumb-bell balloon catheters are not suited to long-term perfusion of kidneys. If an aortic balloon catheter is not properly positioned, it may accidentally occlude the renal artery, mesenteric artery and other blood passages near the branch for the renal artery. These arteries may also become occluded as a result of the shifting of the catheter if the patient moves or is moved or rolled as it is common in medical practice. Presence of an occluding balloon in the aorta downstream of the left ventricle will increase the resistance to the ejection of the blood by the left ventricle (main pumping chamber) of the heart and is highly undesirable in patients suffering from heart failure. By increasing the downstream resistance to blood flow, an occluding balloon increases the workload on the failing heart and, thus, directly undermines the treatment of the heart which usually includes decreasing vascular resistance that the heart must overcome.

Another existing catheter has a perfusion cannula tipped with an occluding inflatable balloon are commonly used to perfuse organs in-situ, and include coronary sinus retrograde perfusion catheters for supplying blood or cardioplegia solution to the heart during cardiac surgery. The balloon on the tip of the catheter is inflated with gas or liquid until the balloon is expanded to form a tight seal between the balloon and the walls of the blood vessel or the body cavity. Perfusate, e.g., blood, saline or other oxygen carrying fluid, is pumped into the main lumen of the catheter at a flow rate needed to achieve the desired organ perfusion pressure. A similar device (Pruitt-Inhara shunt) has been used to protect kidneys from hypotension during aortic surgery.

In current balloon tipped perfusion catheters, the balloon is introduced into a blood vessel and inflated to a relatively-high pressure (significantly higher than the normal blood pressure) until the balloon fits tightly against the blood vessel wall, dilates the wall and totally occludes the vessel passages. The perfusate flow is initiated creating an elevated pressure zone distal of the balloon that is substantially higher than the pressure in the artery proximal to the balloon.

Balloon-tipped catheters can "drift" or migrate proximally (out of the vessel) owing to the distal-to-proximal pressure gradient. The balloon is generally prevented from moving by the friction between the external surface of the balloon and the vessel wall. Ribs, dimples, barbs and other similar features are put on the outer surface of the balloons to increase the friction force and prevent drifting of the balloon in the blood vessel.

If a balloon-tipped perfusion catheter remained inflated in a blood vessel for several days, certain adverse effects would result. The continuous pressure applied by the balloon can damage or completely destroy the endothelium (innermost layer of the blood vessel). Although relatively small areas (less than 3 cm) of the blood vessel stripped off the endothelium are likely to recover over time, blood clots might form in the vessel as the result of the injury and cause acute thromboses. The continuous distention of the wall of an artery by an inflated balloon may prevent oxygen from reaching the walls in contact with the balloon and can result in the transmural ischemia of the wall tissue and tissue necrosis. This condition can lead to the development of an aneurysm, rupture and severe internal injury and bleeding.

If a totally-occluding partition of a catheter is introduced distally to the entrance into an artery, blood flow will completely cease in the branch of the artery proximal to the occlusion. Properties of blood are such that a clot is likely to form in the stagnant pools of blood with no circulation. This is especially likely if the blood is in contact with any material other than the natural internal lining of the vessel. Later, when the catheter is removed, the clot may drift downstream in the perfused or an adjacent artery and can cause a total occlusion of a vital artery and shut-down of blood flow to a vital organ.

In existing perfusion catheters, the catheter is held in place by the same means that partition and seal the perfused organ artery (in most cases an inflatable balloon). In an organ such as a kidney that relies on one major artery for a substantial part of its oxygenated blood perfusion such catheter that seals the renal artery for extended periods of time by distending its walls could damage the artery and kidney. A catheter is needed that seals and unseals the passage of the kidney artery to permit blood to flow naturally to the kidney (when the catheter is unsealed) and, alternatively, to provide perfusion or perfusion from an external blood pump as needed.

A kidney perfusion catheter is needed that may be used during the extended treatment, e.g., several days, of acute hypotension (low blood pressure) resulting from heart failure or to prevent an impeding renal failure in an intensive care unit of a hospital. The catheter is inserted into the patient, for the duration of hypotension that is potentially injurious to the kidney can last as long as two or three days. It was also desired to have a catheter that does not require extensive surgery to be inserted into a patient to the perfused artery to a kidney. The catheter would preferably be introduced and secured using common minimally invasive percutaneous technique by an interventional cardiologist or radiologist in a catheterization laboratory.

SUMMARY OF THE INVENTION

A novel kidney perfusion catheter assembly has been developed having an introducer catheter shaft, a reversible sealing mechanism, a perfusion tip, and a guide wire. The perfusion catheter assembly provides a flow of supplemental blood to increase the local blood pressure in the renal artery and to perfuse the kidney. The perfusion catheter includes an introducer catheter, a perfusion catheter tip and a guide wire. The perfusion catheter assembly is inserted into the femoral artery through an incision in the skin at the groin of a patient. The introducer catheter is maneuvered through the femoral artery into the abdominal aorta and positioned opposite the ostium (entrance) into the renal artery.

The perfusion catheter tip is telescoped from the distal end of the introducer catheter into the renal artery. The introducer catheter has a small diameter that does not substantially obstruct blood naturally flowing through the aorta. The catheter tip has a small diameter that does not substantially obstruct blood naturally flowing from the aorta into the renal artery until the seal mechanism is activated. A blood pump attached to the proximal end of the perfusion catheter assembly provides a flow of blood that streams from the perfusion catheter tip into the renal artery. This stream of blood increases the pressure and volume of the blood flowing through the renal artery and into the kidney.

The perfusion catheter assembly is suitable for long term, e.g., several days or longer, treatment of impaired renal perfusion. The catheter assembly has several distinctive characteristics, including (without limitation and without requirement that all distinctive characteristics be included in each embodiment of the catheter assembly):

a) The catheter assembly is introduced percutaneously via a femoral artery and the bulk of the catheter assembly remains in the femoral artery and the lower aorta. To avoid excessive obstruction of blood flow to lower body and resulting ischemia, the introducer catheter, preferably has an external diameter of 9 or 8 French or less.

b) The catheter assembly is capable of delivering approximately 500 ml/min of blood to the renal artery in conjunction with a peristaltic roller blood pump or a centrifugal blood pump. The blood is pumped from an extracorporeal blood pump, through an inner lumen of an introducer catheter, into a smaller perfusion catheter tip, and is discharged from the perfusion catheter tip into the renal artery. The volume blood flow requires an internal lumen diameter of the introducer catheter sufficient to avoid the need for high pressure and high velocity blood flow that would require the use of high-pressure pump technologies and could damage the blood due to high shear stress resulting from excessive blood velocity.

c) The perfusion catheter tip, which is the portion of the catheter penetrating the renal artery, preferably is of a small outer diameter, such as 6 French or less.

d) A sealing device, e.g., balloon, on the introducer catheter distal edge substantially seals the entrance into renal artery, e.g., at the ostium, to ensure that the perfusion sufficiently increases the blood pressure seen by the kidney without substantially distending the walls of the renal artery. The sealing device also allows for continued blood flow through the aorta to the lower portions of the body (including the legs) and may allow for circulatory flow into the renal artery, around the catheter tip, and into the kidney when inactivated without the removal of the catheter. An additional partitioning device may be added to the catheter tip to dam or partition the renal artery, create additional resistance to the runoff of the perfusion fluid without substantial ally contacting or distending the walls of the renal artery.

e) The catheter tip remains anchored in the renal artery for several days, and should not drift from its position in that artery, even as the patient is moved. Anchoring is achieved by: (a) attachment of the proximal end of the catheter to the skin at the groin; (b) substantial penetration of the catheter tip into the renal artery; (c) bracing of the introducer catheter across the aorta against the aortic wall opposite to the perfused renal artery entrance.

In operation, the kidney perfusion catheter apparatus is introduced into the femoral artery percutaneously, advanced into the aorta and further into the renal artery (tip only) using common methods under fluoroscopic guidance. The catheter includes at least one perfusion lumen for the infusion of blood under pressure. The catheter remains in the renal artery for several days to deliver perfusate to at least one kidney, to protect the kidney(s) from hypotension and normalize renal function. The catheter may have components that secure and immobilize the catheter with the perfusion tip in the renal artery, safely seal and/or partition the renal artery to substantially prevent retrograde flow from that artery into the aorta, and to monitor renal artery pressure in the perfused zone.

Inserting a renal artery perfusion catheter into the human aorta and into renal arteries is difficult. The renal arteries are approximately 4 to 6 mm in diameter in an adult. The aorta is 20 to 25 mm in diameter. The renal arteries branch from the aorta at an angle of 90 to 60 degrees slanted down towards the patient's legs. When inserted into the femoral artery at the groin, the catheter must turn sharply to enter the renal artery. In a renal artery with arteriosclerosis the plaque tends to concentrate in the area of the ostium or entry from the aorta into the renal artery. If the plaque is disturbed and separated from the vessel wall it may float into the kidney and cause severe complications.

A guide wire and guiding catheter have been used to insert catheters that engage and cross into the renal artery for diagnostic catheterization and angioplasty. A guiding catheter is generally a preshaped plastic tube that can be straightened when it is introduced into the femoral artery via a straight sheath catheter. The internal lumen of the catheter houses the guide wire that forces the catheter to remain straight as the catheter and the guide wire are moved through the femoral artery and into the aorta. Once the distal tip of the sheath catheter has been positioned in the aorta and in the vicinity of the renal artery, the guide wire moves axially out of the catheter. The catheter has substantial material memory to resume (recoil) into its curve when it is in the aorta and has enough space to make a turn. A relatively-stiff guide wire can assist in straightening and recoiling of the catheter as needed to traverse the vascular passage. The preshaped curve, e.g., a J-hook or a Cobra hook that spans the diameter of the aorta, of the introducer catheter makes possible the turn that the perfusion catheter has to make to engage the renal artery ostium in the wall of the aorta and to provide a bias (due to the resilience of the hook) that forces the perfusion catheter against the ostium of the renal artery.

In addition, the perfusion catheter would preferably be placed in the renal artery at a catheterization laboratory, but the perfusion does not start until the patient is moved to the intensive care unit (ICU) area of the hospital. Moving a patient with an external perfusion system attached and pumping blood is possible, but presents a logistical challenge. The present perfusion catheter assembly allows for a procedure of inserting the catheter into the renal artery, moving the patient to an ICU, and starting perfusion of the kidney using the catheter after the patient has been safely placed in the ICU.

DETAILED DESCRIPTION OF THE DRAWINGS

Figure 1:
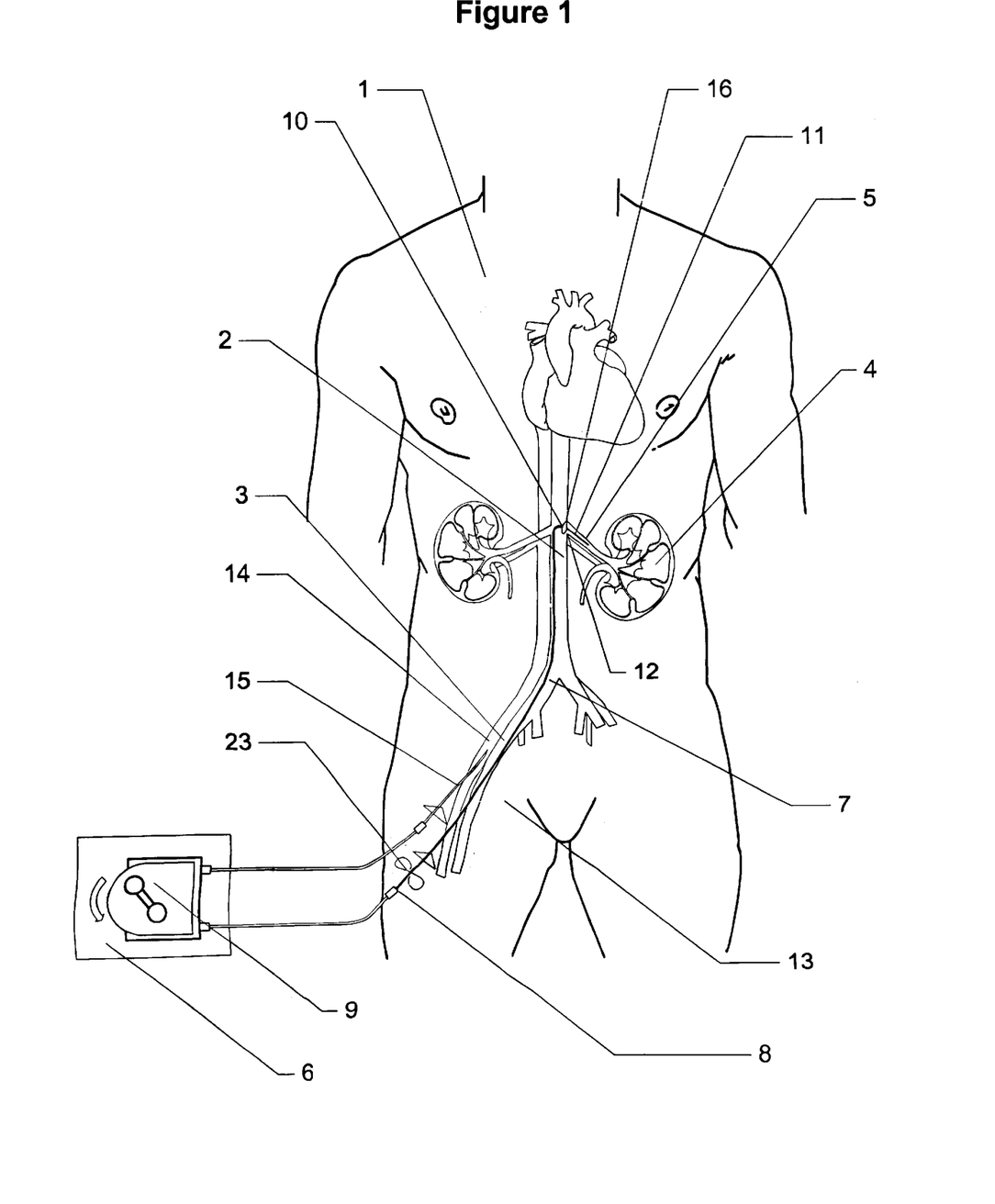
FIG. 1 is a schematic diagram of a kidney perfusion system for drawing blood from a human body, increasing the pressure of the drawn blood with a pump and piping the blood to the renal artery to increase the local blood pressure at the inlet to a kidney.

FIG. 1 is a schematic diagram of a patient 1 having an aorta 2, a femoral artery 3, a kidney 4 and a renal artery 5. The patient is suffering from impaired renal perfusion and is being treated using a clinical in-situ kidney perfusion apparatus 6. The apparatus includes a renal artery perfusion catheter 7 having a proximal end 8 attached to a blood pump 9 and a distal end 10 positioned at the inlet (ostium) of a renal artery 5 to one of the kidneys 4.

Attached to the distal end 10 of the catheter 7 is a catheter tip 11 that extends into the renal artery 5 approximately 2 to 6 centimeters past the ostium 12 of the renal artery. As the perfusion catheter 7 is moved from the insertion point at the groin 13 and through the femoral artery 3, into the aorta 2, it makes a sharp turn at the renal artery branch, passes through the ostium 12 and into the renal artery 5.

Blood, at a higher pressure than the patient's blood pressure, is supplied to the perfusion catheter by the blood pump 9 which is connected with flexible tubing to the proximal end 8 of the catheter 7 with a locking connector. In this embodiment the supply of blood to the pump is drawn from a femoral vein 14 of the patient 1. In other embodiments blood could be drawn from other veins or arteries or from the same femoral artery into which the perfusion catheter is introduced in which case the perfusion catheter 7 may also serve as catheter to draw blood for the pump 9. In the preferred embodiment blood is withdrawn using a cannula catheter 15 inserted into the femoral vein. The pump increases the kinetic energy of the blood, e.g., increases the pressure and/or velocity of the blood, and passes the blood to the perfusion catheter 7 which ejects the blood into the renal artery from tip 11 of the catheter. The blood ejected from the catheter tip increases the pressure of the blood flowing through the renal artery to the kidney. Using the perfusion apparatus 6 (which includes perfusion catheter 7, pump 9, and cannula catheter 15), the blood flow entering the kidney 4 has sufficient flow and pressure to cause the kidney to resume normal functioning, including removing excess body fluids, sodium and toxins, and increasing urine flow. In addition, a partitioning and/or sealing element 16 on the shaft of the catheter 7 at the distal end 10 prevents injected blood from running off into the aorta where pressure is lower.

Figure 2:
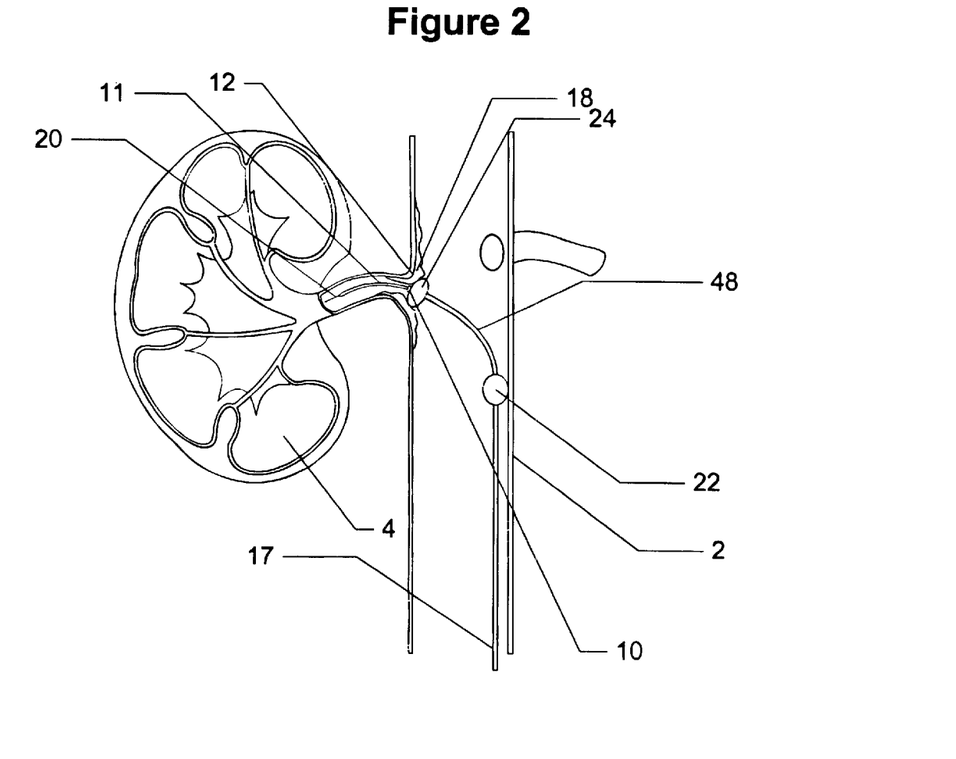
FIGS. 2 and 3 are cross-sectional diagrams showing two procedures for inserting a catheter into a renal artery.
Figure 3:
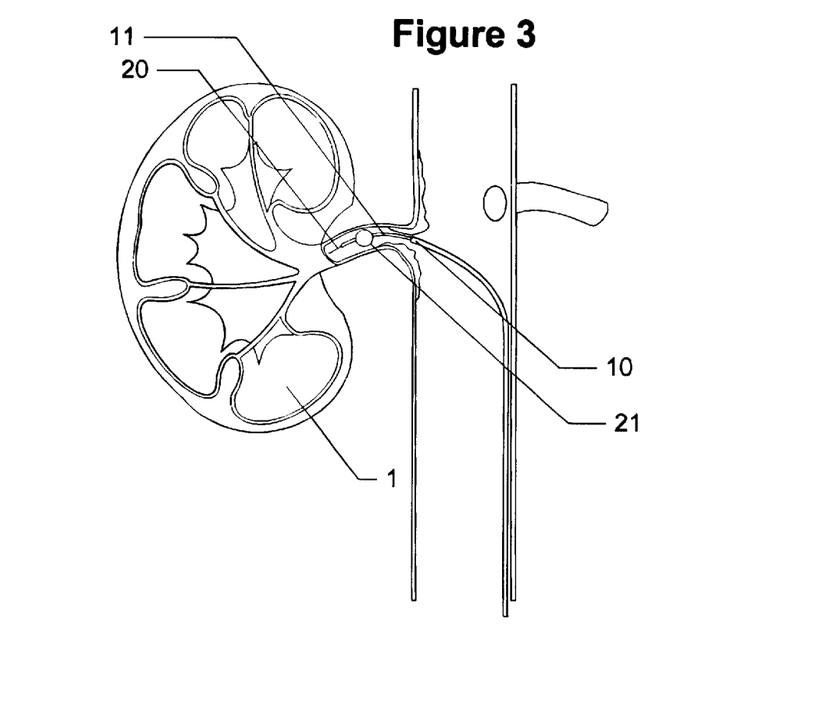

FIGS. 2 and 3 illustrate two embodiments of a renal artery perfusion catheter 7 and partitioning element 16. An introducer (shaft) component of the catheter 17 may be a hollow tube similar to a common guiding catheter. The shaft can be preshaped to facilitate positioning at the ostium 12 of the renal artery. The ostium may have plaque deposits 18 which the catheter tip 11 must navigate through to reach the renal artery. An introducer catheter component 17 of the perfusion catheter has its distal end 10 that is positioned against the ostium of the renal artery but does not substantially penetrate the ostium. Moreover, it is desirably that the catheter not break off the plaque as it enters the ostium as plaque particles could enter the renal artery and block the kidney. The introducer catheter is not likely to cause plaque separation or damage the renal artery, because it does not enter that artery.

The introducer catheter 19 has a tubular body and is a shaft through which other components of the perfusion catheter assembly, e.g., guide wire and catheter tip, can be maneuvered to a body organ, and through which flows the prefusate, e.g., blood. The perfusion catheter tip 21 is housed within a distal portion of the introducer catheter and the tip extends from the introducer component into the renal artery. A sealing balloon 24 on outside of the distal portion of the introducer catheter is an embodiment of a sealing device 16 that is inflated in the aorta positioned to overlap and block the entrance (ostium) to the renal artery. A partitioning balloon 21 on the catheter tip resides in the renal artery and may function to dam or partition the renal artery to prevent (or at least reduce) retrograde blood (perfusate) flow from the renal artery back into the aorta.

The perfusion tip 11 (having a diameter of 6 French of less) is substantially smaller in diameter than the introducer catheter (having a diameter of 9 or 8 French or less). The perfusion tip fits coaxially in the introducer catheter cavity, and is generally confined to the distal end of the introducer catheter. The tip 11 can be advanced through the introducer catheter 19 deep into the renal artery 5. The tip 11 is withdrawn into the introducer catheter when the perfusion treatment is completed, which may be several days after insertion of the catheter. Substantial depth of penetration of the perfusion catheter into the renal artery ensures that the tip 11 and other catheter components at the distal end 10 are not separated and disengaged as the patient is moved.

A flexible guide wire 20 facilitates the introduction of the catheter tip. The guide wire can be threaded through a main perfusion lumen or a pressure measurement lumen of the multi-lumen introducer component 17 and the guide wire may extend farther into the tip 11. As seen in FIG. 2 the introducer catheter component 17 is held in place by the telescopic perfusion tip 11 in the renal artery and the force of the introducer catheter 17 biased against an opposite wall of the aorta 2.

The catheter assembly is prevented from moving laterally within the femoral artery and aorta by an attachment to the skin such as suture at the proximal end 8. In a patient with a beating heart, the wall of the aorta is in constant motion. The aorta expands and contracts following the ejection of blood by the left ventricle of the heart. The catheter loop or turn 48 spans the diameter of the aorta and is biased against opposite sides of the aortic wall. The loop and the telescopic design of the catheter tip 11 work together to follow the contraction and expansion of the aorta and prevent the damage to the renal artery. The catheter shaft 19 of the introducer catheter has a hook shape 48 spanning aorta and acts as a spring to store and release energy in synchronization with the pressure pulses in the blood caused by the beating heart. Hook 48 acts as a spring and like a spring can have shapes other that the one shown for the preferred embodiment including ones with coils and wide loops spanning across the aorta.

An inflatable bracing balloon 22 or other bracing mechanism may be used to assist with catheter positioning. The inflated bracing balloon on the introducer catheter pushes the catheter shaft away from the aortic wall and braces the assembly. The catheter shaft is prevented from recoiling and moving longitudinally by the attachment to the skin 23 at the proximal end 8 and the telescopic tip 11 at the distal end 10. Thus, the perfusion catheter is prevented from dislodging if the patient is moved.

The leading (distal) edge of the introducer catheter 19 is pressed against the renal artery ostium 12. While in the aorta, the sealing balloon 24 is inflated with fluid and pressed against the ostium to soften the pressure exerted by the tip against the ostium and to prevent it from damaging the renal artery. The sealing balloon 24 also substantially seals the renal artery and prevents the infused blood delivered from the infusion catheter tip from leaking out of the renal artery.

FIG. 3 shows a partitioning balloon 16 integrated in the catheter tip 11. The balloon can be inflated when the extracorporeal perfusion is desired and deflated to restore the natural circulation to the kidney. The balloon 16 can be inflated by gas or liquid from the external source or can be of the autoinflation type. A lumen extending through the tip and inducer catheter provides a fluid passage for inflating the balloon. The balloon may have an inflated diameter sufficiently to prevent substantial retrograde blood flow from the renal artery into the aorta. The inflated balloon diameter may be sufficiently small so that it does not excessively distend the renal artery or plaque in the ostium.

Figure 4:
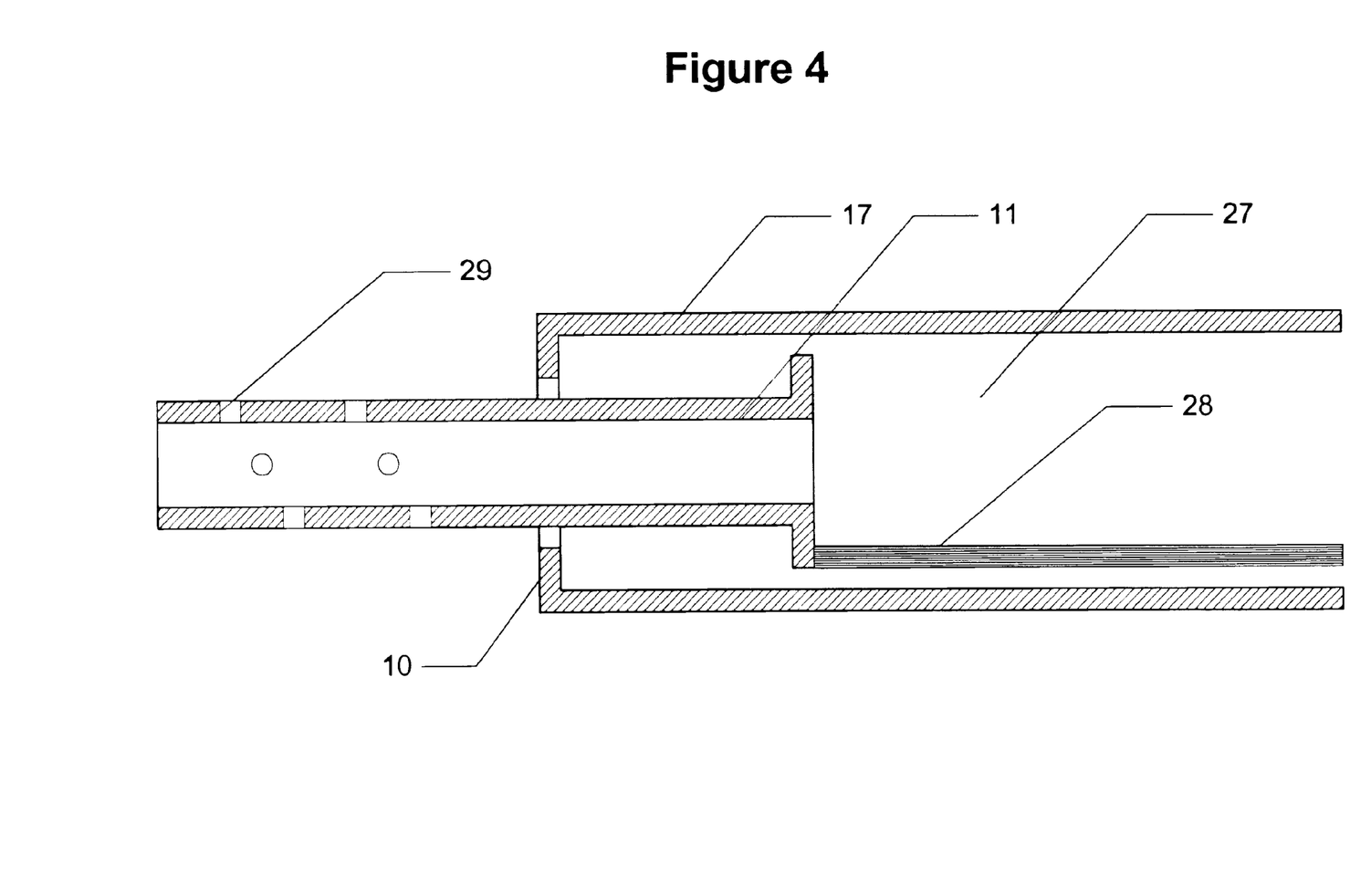
FIGS. 4 to 7 are cross-sectional diagrams showing various embodiments of catheter tips.
Figure 5:
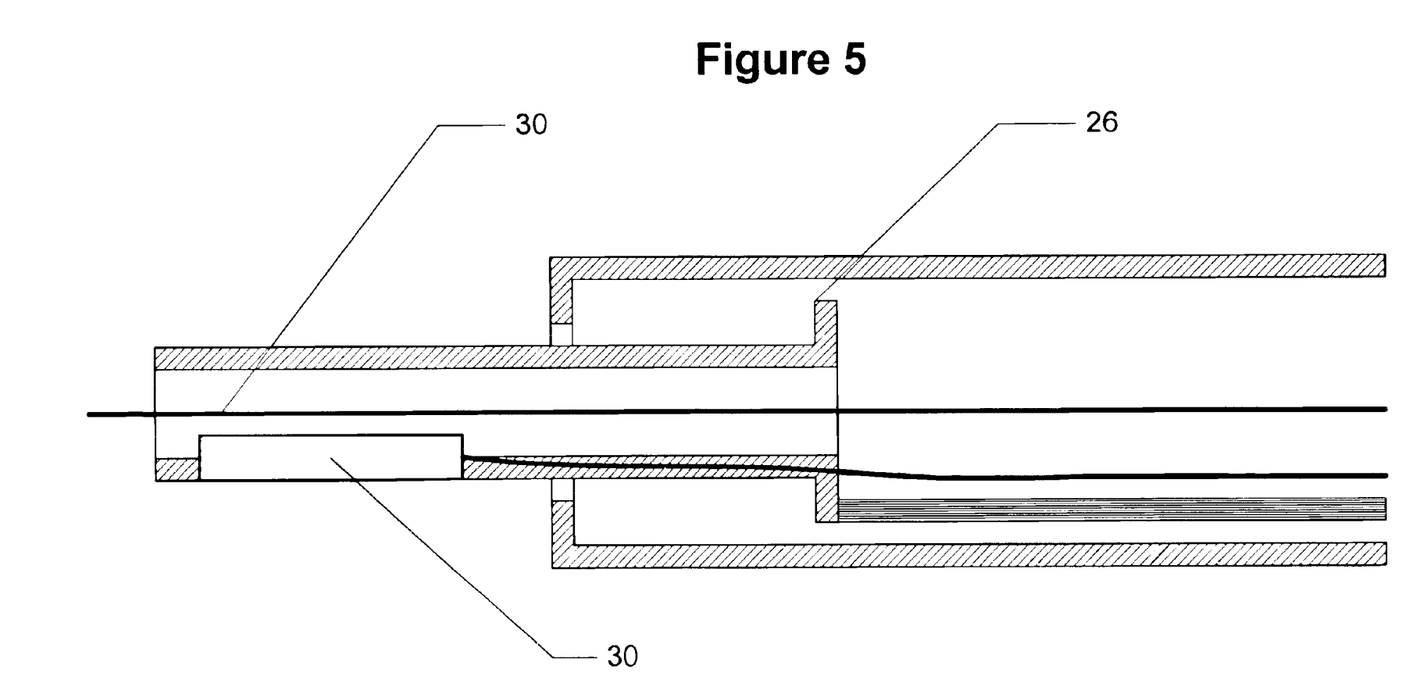

FIGS. 4 and 5 illustrate alternative embodiments of the perfusion catheter tip 11. The tip 11 of the catheter may have a diameter of 6 French (slightly less than 2 mm) or less. The tip is a relatively short tube that may have a flange 26 at its proximal end to engage the end of the introducer catheter and prevent the tip from be entirely ejected from the introducer catheter. Alternatively the tip can be prevented from extending too far by the limit on the travel of the torque wire 28 at the proximal end of the catheter 8. The catheter tip 11 moves coaxially in the distal end of the introducer catheter 17. The tip may be retracted within the introducer catheter or telescopically extended from the distal end of the introducer catheter component.

The introducer catheter component (9 or 8 French or less) requires substantial structural strength and this strength requirement will affect how thin the catheter shaft wall can be made without the catheter collapsing or kinking inside the aorta. Additionally, the introducer catheter must have sufficient thickness to accommodate features, such as the balloon inflation and pressure measurement lumens.

Presently, it is believed that the introducer catheter should have a diameter of substantially more than 6 French (Maximum size allowed to penetrate the renal artery) catheter to allow sufficient perfusion flow lumen. The introducer catheter must reach from the groin to the renal artery (65 cm), and have a sufficient cross-sectional area to accommodate an internal perfusion lumen of more than 1.5 mm diameter or preferably 1.85 mm diameter. If the introducer catheter is 6 French or less then the blood flow through the catheter would experience substantial viscous and wall friction losses. Calculations and experimental data show that to deliver 500 mL/min of blood (a reasonable flow to perfuse one kidney) via such long narrow lumen that can be reasonably designed inside the 6F catheter shaft, the blood pump will need to develop pressures in excess of 100 psi in the blood flow. This is undesirable for safety and economic reasons.

It is desired that the perfusion pump pressure is limited to 20 to 30 psi commonly used in medical devices of this kind. Resistance to laminar flow of a viscous liquid in a long smooth tube is directly proportional to the length of the tube and inversely proportional to the fourth power of the internal radius of the tube. A decrease of the internal lumen of the catheter by the factor of two will result in the increase of the blood pump pressure needed to sustain the required perfusion flow by the factor of 16. The need for reduced pressure in the introducer catheter can be obtained by increasing the diameter of the introducer catheter to 8 or 9 French. These larger introducer catheters should deliver adequate perfusate blood flow from the blood pump, through the femoral artery and aorta and to the catheter tip 11, without excessive viscous friction losses.

FIGS. 4, 5, 6 and 7 show a catheter embodiment having a relatively short tip section 11 (approximately 2 to 6 cm) of the overall catheter length (over 35 cm, and typically 65 cm, for example). The tip is thin to penetrate the renal artery without distending the ostium or the renal artery, and to prevent the dislodging of plaque from the renal artery or ostium. Tip 11 is an extendible hollow tube that fits within the distal end of the introducer catheter.

The catheter assembly is inserted into the aorta in the collapsed configuration with the tip retracted and any balloon deflated or other sealing/partitioning devices deactivated. The introducer catheter is free to recoil when it enters the large abdominal aorta, which has a large diameter in which the catheter can uncoil.

The introducer catheter can be positioned against the ostium of the renal artery using a fluoroscopic technique. Small amounts of contrast fluid can be injected into the catheter through the lumen 27 to illuminate the renal artery. In addition a guiding wire 20 is advanced through the same lumen into the tip 11 and the wire is advanced farther into the renal artery to assist placement of the catheter tip. A radio opaque marker may be placed on the leading edge of the tip 11 to make it visible during the insertion.

The catheter 7 is properly positioned opposite to the renal artery ostium. The guide wire 20 is advanced substantially into the renal artery. The perfusion tip 11 is advanced over the guide wire into the renal artery. The tip advances forward by applying pressure to a torque wire 28 that is flexible to follow the curve of the catheter. However, the torque wire is sufficiently rigid to avoid kinking under the substantial forces needed to overcome friction and push the telescopic tip forward. The torque wire may be a coated metal spiral to better resist kinking. Alternatively, the torque wire may be a braided or wire reinforced thin wall plastic tube. A tubular design for the torque wire has an additional advantage of providing useful hollow inner space that could be utilized for fluid, electric wire or optical communication fibers.

In addition, the external surface of the catheter tip 11 maybe slippery or coated with a material that reduces friction to facilitate the movement of the tip inside the introducer catheter and through the renal artery. When sufficiently advanced into the renal artery, the telescopic tip is locked in position by fixing the proximal end of the torque wire 28 with a torque nut or other anchor. The proximal end of the torque wire is exposed from the proximal end 8 of the perfusion catheter 7, and the torque wire can be equipped with a grip or a handle for use by the physician. A circular seal, such as an O-ring, around the torque wire at the proximal end of the perfusion catheter 7 can be used to prevent blood from leaking out of the catheter around the torque wire.

Mechanical coupling of the torque wire to the tip could be such that when the torque wire is rotated at the proximal end the telescopic tip will change its orientation abut the catheter shaft axis. Rotation or the torquing of the wire allows the tip 11 to be positioned to enter the renal artery, without repositioning the introducer catheter. If the attachment of the torque wire to the proximal end of the tip is off-center the tip (as shown in FIGS. 4 and 5) the tip can be rotational torqued about its axis. Also, the flange 26 could be slightly asymmetric in relation to the axis of the tip so that if the tip is rotated inside the introducer shaft its projection angle will change.

Flange 26 on the proximal end of the tip 21 seals the tip against the inner wall of the introducer catheter. In other embodiments flange 26 may be a O-ring. In other embodiments flange may not be needed at all and the tip 11 can be inserted flush and slide against the inner wall of the introducer shaft 17. This seal can be tight or form a small gap. The perfusion catheter can tolerate small leaks of perfusate and still properly perfuse a kidney. To reduce the velocity of the jet of the blood stream (or other perfusate) exiting from the catheter tip 11 and to protect the renal artery, the tip may be perforated with multiple holes 29 that are laser drilled in the walls of the tip 11.

A micro-pressure sensor 30 may be incorporated in the tip to measure renal artery pressure. The sensor can be of electronic type such as commonly used in pressure sensing guide wires or an optical sensor such as RJC Enterprises from Woodinville, Wash. An optical sensor has the advantage of immunity to electromagnetic interference and the inherent electric safety. Optical fibers of 100 micron diameter are commonly available for catheter applications. Fibers or wires can be incorporated inside the torque wire 28 and routed outside of the proximal end of the catheter 7 for connection to an instrument such as pressure monitor or controller of the perfusion (blood) pump 9. Alternatively, an additional channel can be incorporated into the wall of the tip 11 to provide fluid communication with an internal channel inside the torque wire 28. At the proximal end of the catheter 8 the channel is connected to a common fluid filled blood pressure sensor, or other device.

Internal lumen of the tip forms a continuous conduit between the internal cavity of the renal artery and the proximal end 8 of the catheter 7 that is outside of the body and provides the access passage for the operator. Instruments other than a guide wire can be also introduced into the renal artery via this conduit.

Figure 6:
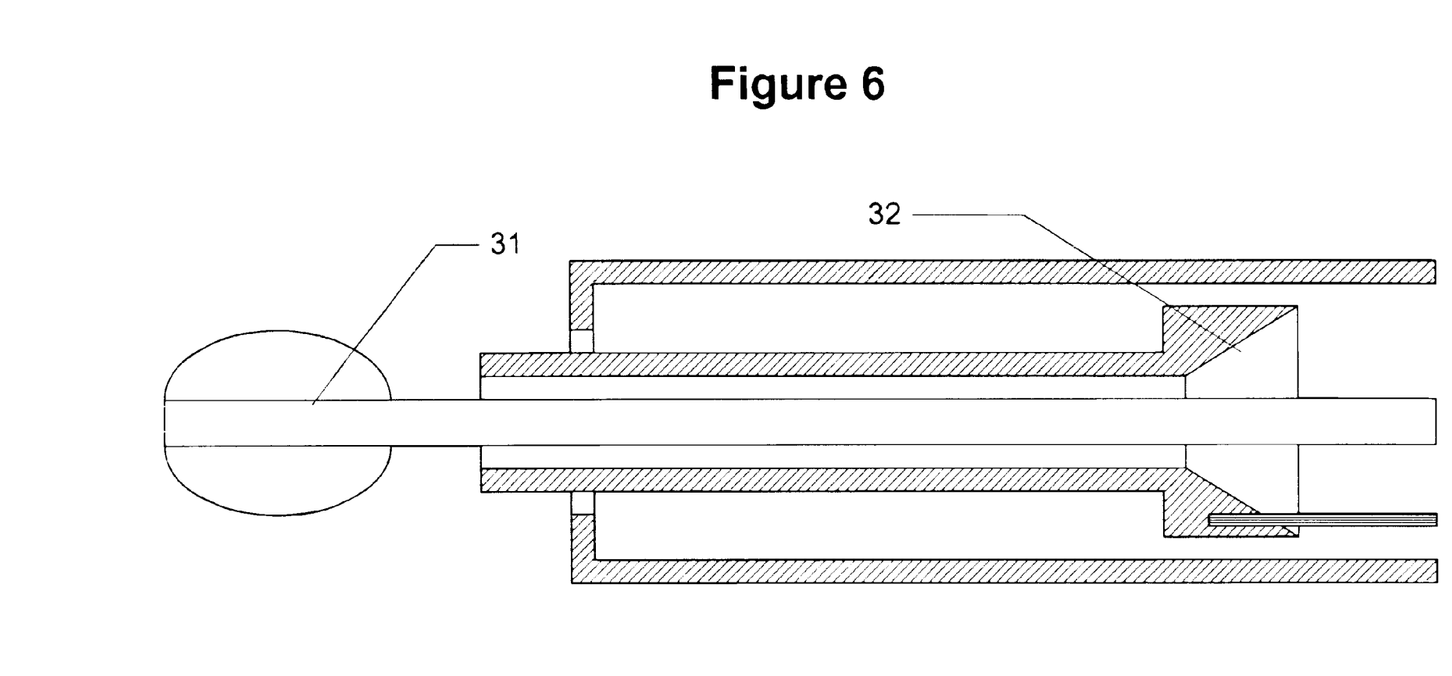

FIG. 6 shows how a common angioplasty dilatation catheter 31 can be advanced into the renal artery. This method could be used if the plaque growth 18 at the ostium of the renal artery is advanced and occludes more than approximately 75% of the cross section area of the artery. The renal artery in an adult human is approximately between 4 and 6 mm in diameter. Advanced renal artery disease can reduce the diameter of the renal artery and prevent the 2 mm outside diameter (OD) tip 11 of the perfusion catheter from penetrating the renal artery past the ostium. When advanced renal artery disease is present, an angioplasty dilatation catheter can be advanced first, the dilatation partitioning balloon is then inflated, and the renal artery expanded sufficiently to allow the perfusion catheter tip 11 to pass through the artery.

A tapered aperture 32 is shown in FIG. 6 to assist guiding wires 20 and other instruments into the inner lumen of the tip 25. To minimize resistance to perfusate flow, the taper may have a profile known to minimize turbulence, such as for example a 10-degree slope to the taper.

Figure 7:
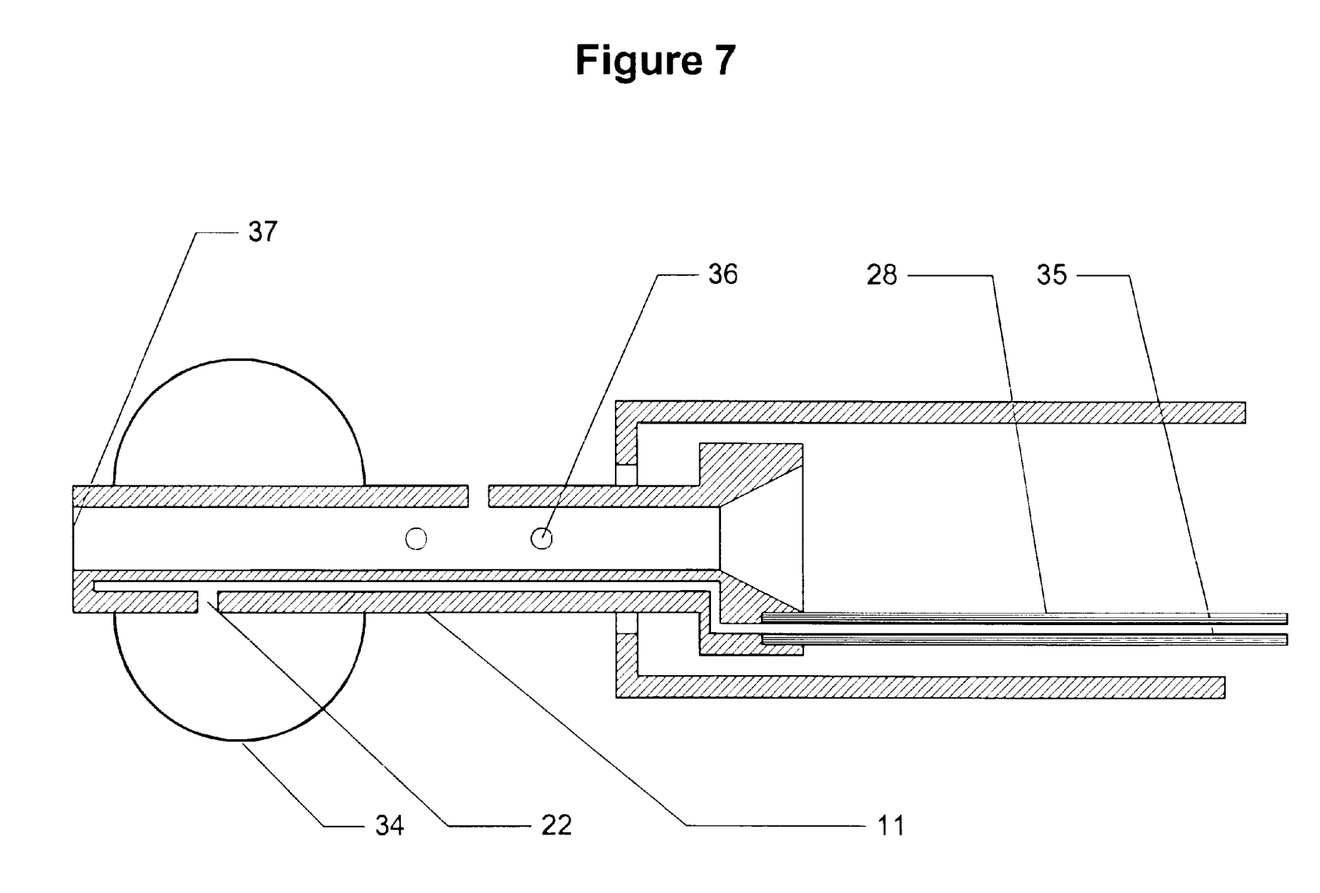

FIG. 7 discloses another embodiment of a partitioning device for the renal artery. An inflatable balloon partitioning 34 is attached to the tip 11 of the catheter. When the perfusion system is not pumping blood, the partitioning balloon is deflated and does not present a substantial resistance to blood flow through the renal artery from the aorta. As a result, natural perfusion of the kidney can be partially restored since the catheter tip is substantially narrower that the human renal artery (2 mm OD vs. 4 to 6 mm ID).

To perfuse the kidney, the partitioning balloon 34 is inflated to substantially block the natural flow. The kidney is supplied with blood by the perfusion pump at an elevated pressure. Balloon 34 is in fluid communication with the internal cavity 35 of the torque wire 28 via the conduit in the wall of the tip 21. At the proximal end 8 of the catheter, a lumen inside the torque wire can be connected to the commonly-known means to inflate and collapse the partitioning balloon. Alternatively, a separate inflation tube can be threaded inside the main lumen of the catheter shaft.

It is desirable to have a perfusion catheter that partitions the renal blood vessel without subjecting the vessel wall to significant stress, prolonged contact over a large area of the vessel wall, and will not create stagnant blood zones. Such a catheter could be used to safely perfuse an organ for a significant periods of time. The catheter does not use the occluding or partitioning balloon 34, to retain the position of the catheter in the renal artery but only to prevent the backflow from the renal artery.

The partitioning balloon 34 can fully expand without coming into substantial contact with the vessel walls of the artery. For example, the balloon may be a substantially inelastic material, such as nylon or urethane, that does not expand beyond a programmed diameter when inflated to the working pressure. The external diameter of the partitioning balloon 34 could be, for example, approximately 4 mm so that it does not fully obstruct the artery when inflated. Alternatively, the balloon could be made of an elastic material such as silicone with known properties so that the diameter of the balloon when inflated could be calculated from the injected volume or inflation pressure.

For effective organ perfusion the renal artery vessel need not be completely occluded. It is sufficient to assure that the adequate blood pressure is generated distal to the partition. If, for example, 10% of the infused blood leaks out of the high pressure distal zone of the partitioned artery vessel, i.e., retrograde flow, into the low pressure of the aorta, adequate perfusion flow to the kidney can be maintained by automatically increasing the pump speed and flow delivery by approximately 10%, maintaining the desired pressure. The net resulting perfusion pressure and flow delivered to the organ will be the same. If the retrograde leakage is intentionally allowed through a narrow gap between the balloon 34 and the vessel wall of the renal artery, the area of the vessel proximal to the balloon will be continuously washed by the retrograde blood flow. This "blood washed" design will prevent both ischemia and damage of the vessel wall and also prevent the formation of stagnant zones proximal to the balloon.

Another way to eliminate a stagnant zone of blood in the renal artery is to include in the catheter tip a number of small orifices 36 proximal to the partitioning balloon 34. The cumulative cross-sectional area of these small orifices will be substantially smaller than the cross section area of the main catheter outlet 37 which directs perfusate to the kidney. Most of the perfusion flow will follow the path of minimal resistance through the main outlet 37 and flow towards the kidney. There will be some minimal blood flow that will be diverted through the small orifices and into the renal artery. This flow amount can be made as low as 5–10% of total perfusate flow but sufficient to prevent clotting of blood in the renal artery.

Figure 8:
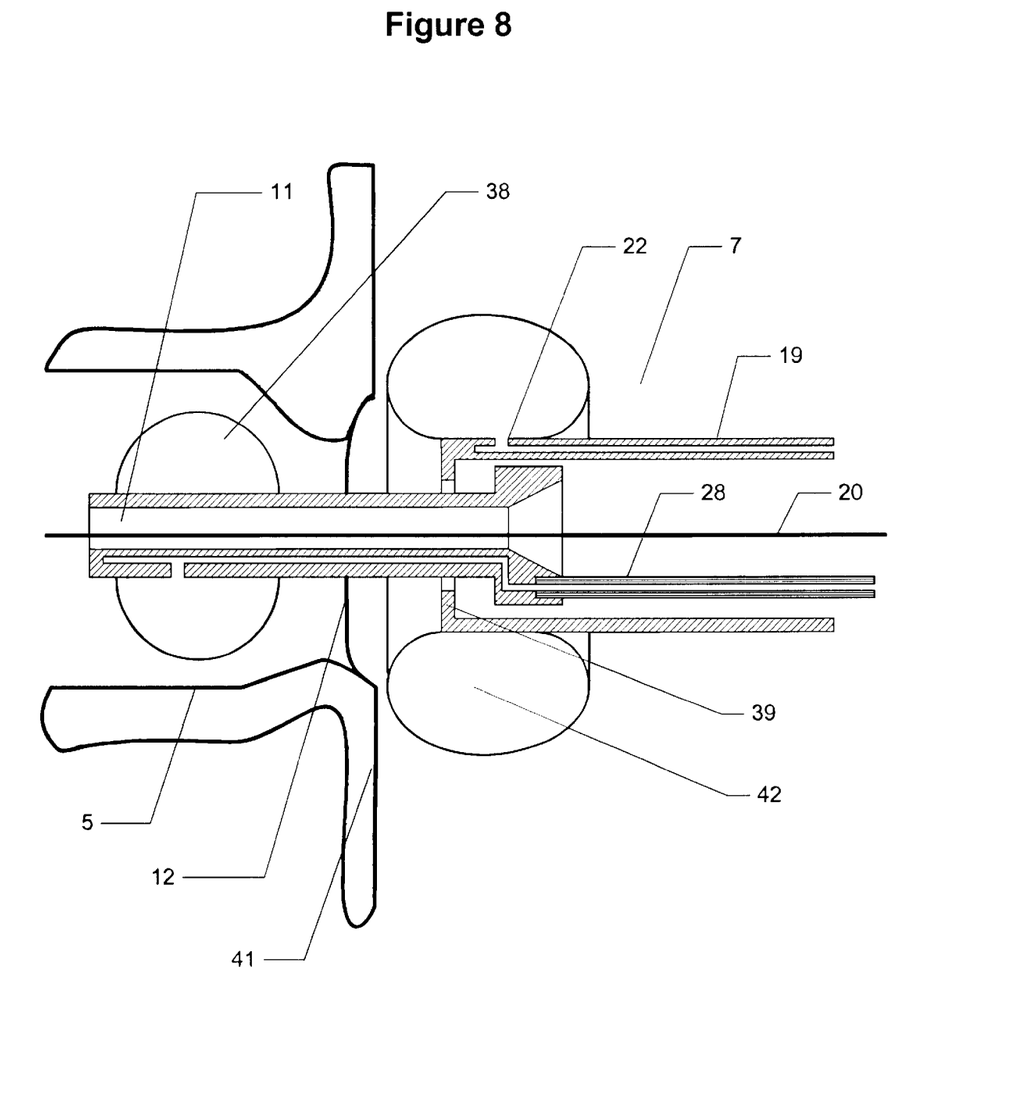
FIG. 8 is a cross-sectional diagram of a catheter tip positioned at the inlet to a renal artery.

FIG. 8 discloses an embodiment of the renal artery ostial seal. Both the partitioning balloon 38 on the perfusion tip 11 and the sealing balloon 42 on the distal end of the introducer component 39 are used to contain the pressure in the renal artery 5. The inflatable balloon 42 is attached to the distal end 39 of the introducer catheter shaft 19. The balloon 42 is in fluid communication 22 with an internal channel in the wall of the catheter shaft 19. A common balloon inflation apparatus is connected to the proximal outlet of this channel at the proximal end of the catheter.

The aortic wall 41 and the renal artery 5 form the ostium 12 of the renal artery. The leading edge (distal end) 39 of the introducer catheter 19 is brought against the renal artery ostium with the help of a guide wire 20. With the guide wire in place, the telescopic catheter tip 11 is advanced into the renal artery using the torque wire 28. When the tip is advanced into the renal artery to the desired depth, the torque wire is secured at the proximal =end of the perfusion catheter. The catheter assembly 7 is locked in place but not sealed. The balloons 38 and 42 are deflated and are substantially flat against the corresponding surfaces of the catheter and the catheter tip.

When the extracorporeal perfusion of the kidney is desired, the perfused renal artery is substantially sealed from the aorta by inflating the balloons 38 and 42. Balloon 42 is inflated with gas or an appropriate liquid such as saline. When inflated, the balloon 42, which is in the aorta, expands substantially radially to cover the area around the ostium, but is sufficiently small so as to not substantially disrupt blood flow through the aorta and create additional load on the heart. It is desired that the forward surface of the balloon 42, when inflated, extend axially beyond the distal edge of the introducer catheter to cushion the aorta and renal artery, and protect the ostium. The hook shape of the loop section 48 of the introducer catheter 19 is spring loaded against the opposite walls of the aorta and this spring loading biases the introducer the distal edge of the introducer catheter safely against the ostium. When biased against the ostium, the sealing balloon 42 blocks the renal artery inlet to form a seal and to prevent retrograde flow during perfusion.

It is significant that the bend 48 of the catheter shaft 19 acts as a coiled spring when braced against the opposite wall of the aorta. If for some technical reason the pressure inside the renal artery increased dramatically, the buildup of pressure will push the cushion balloon 42 away from the ostium. As a result pressure in the renal artery will be substantially reduced and the kidney will be protected from severe barotrauma.

Figure 9A:
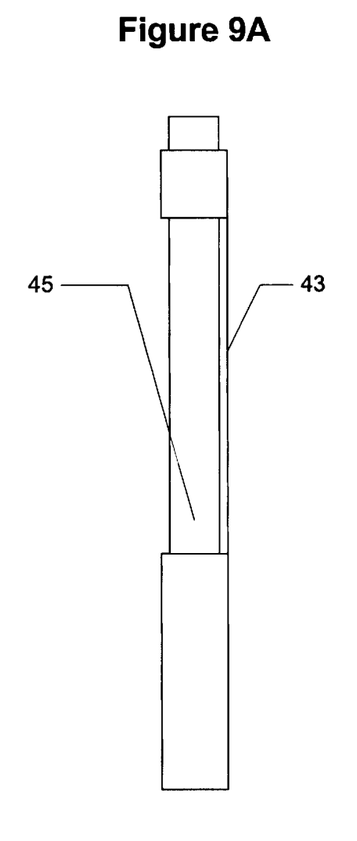
FIGS. 9A, 9B and 9C are diagrams of a catheter bracing mechanism embodiment.
Figure 9B:
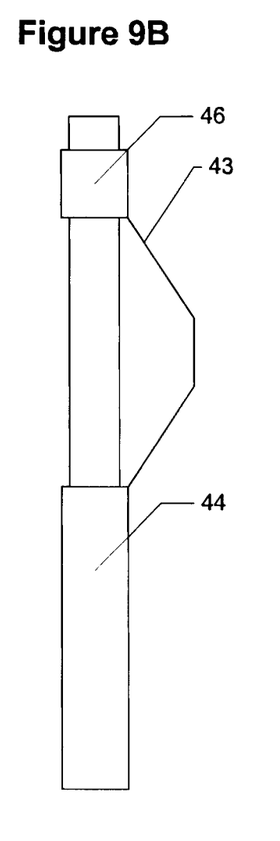
Figure 9C:
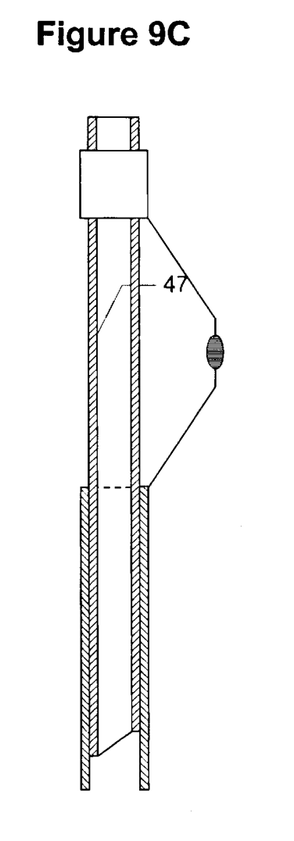

FIGS. 9A, 9B and 9C disclose an alternative embodiment of the catheter brace 43. A thin tubular sheath 44 overlaps the catheter shaft 45. The sheath slides over the catheter shaft and can be advanced forward from the proximal end of the catheter by the operator and secured there by common fixation means. One end of the brace 43 is attached to the sliding sheath 44, another end to the catheter shaft with the fixed attachment 46. When advanced forward the sheath 44, pushes on the brace plate 43 that is preshaped to collapse is a desired fashion. Brace 43 pushes on the wall of the aorta and creates the desired tension. The brace assembly may include more than one brace plates such as 43 to brace the catheter against different walls of the aorta and improve the positioning. A radio opaque marker 47 can be placed on the brace to enable operator to see that the brace is deployed correctly. Alternatively, the proximal end of the brace can be attached to the catheter shaft and the distal end could be allowed to slide over the catheter shaft. A commonly known pull wire technique could be employed to pull on the distal sliding attachment and collapse the brace.

Figure 10A:
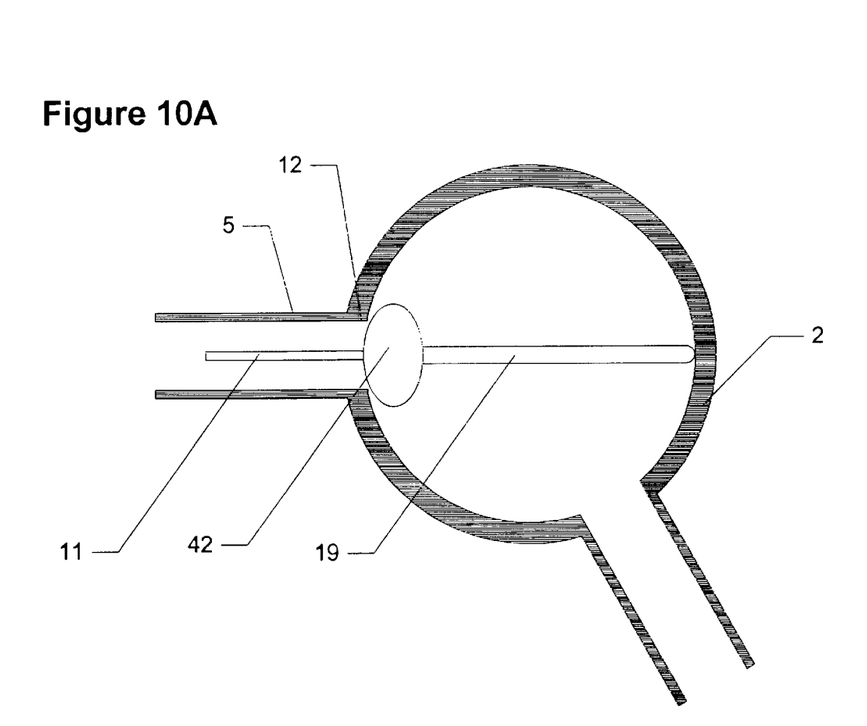
FIGS. 10A and 10B are cross-sectional diagrams of renal arteries, aorta and catheter embodiments when viewed from the top of the body.
Figure 10B:
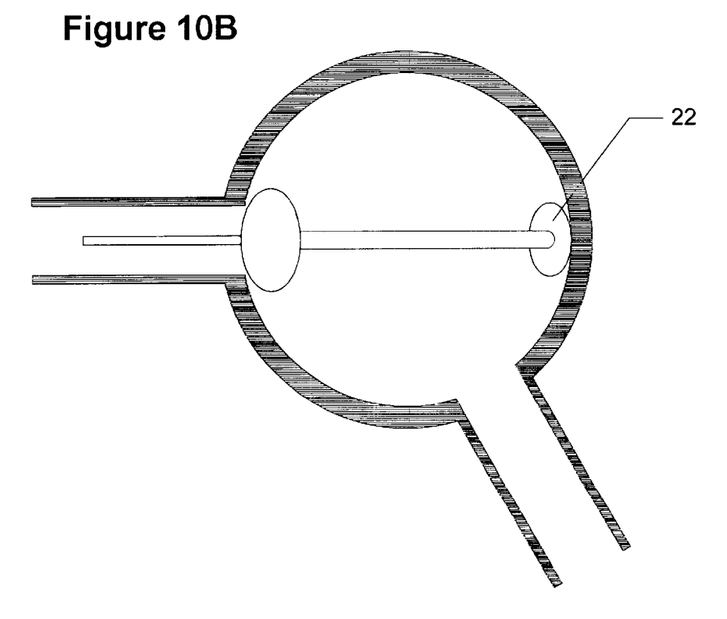

FIGS. 10A and 10B show the cross section of the aorta at the level of renal arteries. The introducer catheter component 19 is braced against opposite sides of the aortic wall to hold its distal edge at the entrance to the renal artery 5 with an inflated bracing balloon 22. The sealing balloon 42 is in the aorta 2, occludes the ostium 12 and cushions the force of the catheter against the ostium. The catheter tip 11 is advanced into the renal artery for perfusion.

The invention has been described in connection with what is presently considered to be the preferred embodiments. The invention is not limited to the disclosed embodiments, but, on the contrary, covers various modifications and equivalent arrangements included within the spirit and scope of the appended claims.

What is claimed is:

1. A method of perfusion of a kidney in a patient having a beating heart, using a perfusion catheter assembly having an introducer catheter and a perfusion catheter tip extending from a distal end of the introducer catheter, and comprising:

a. inserting the introducer catheter into an artery of the patient, maneuvering the perfusion catheter through the aorta and towards the renal artery of the kidney;

b. positioning the distal end of the introducer catheter in the aorta proximate to an inlet to the renal artery;

c. inserting the perfusion catheter tip extending from the introducer catheter into the renal artery, wherein said catheter tip has an inlet proximate a distal end of the introducer catheter;

d. delivering perfusate though the introducer catheter, into the inlet of the catheter tip, through the perfusion catheter tip and into the renal artery to perfuse the kidney, and e. at least partially blocking the inlet to the renal artery with a sealing device entirely in the aorta and attached to the distal end of the introducer catheter, wherein said sealing device is sufficiently large to substantially seal the inlet to the renal artery and sufficiently small to avoid substantially disrupting blood flow through the aorta.

2. A method of perfusion a kidney as in claim 1 further comprising the step (f) of extending a guide wire to the renal artery before positioning the introducer catheter proximate the renal artery or extending the perfusion catheter tip into the renal artery.

3. A method of perfusion of a kidney as in claim 2 wherein step (d) is performed while a partitioning device substantially blocks retrograde flow from the renal artery.

4. A method of perfusion of a kidney as in claim 1, wherein step (e) includes blocking the inlet to the renal artery to prevent retrograde perfusate flow to the aorta from the renal artery.

5. A method of perfusion of a kidney as in claim 1 wherein the perfusion catheter tip has a diameter substantially less than a diameter of the renal artery, and steps (c) and (d) and (e) are performed without distending the renal artery.

6. A method of perfusion of a kidney as in claim 1 wherein the diameter of the perfusion catheter tip is 6 French or less, and the diameter of the introducer catheter is 9 French or less, and step (c) is performed by telescoping the perfusion catheter tip from a distal end of the introducer catheter.

7. A method of perfusion of a kidney as in claim 1 wherein a cushion balloon attached to the introducer catheter rests against a wall of the aorta opposite to the perfused kidney to assist in retaining the positioning of the introducer catheter proximate to the inlet to the renal artery and sealing of the inlet.

8. A method of perfusion of a kidney as in claim 1 wherein a catheter brace attached to the introducer catheter rests against a vessel wall of the aorta to assist in positioning the distal end of the introducer catheter proximate to the inlet to the renal artery.

9. A method of perfusion of a kidney of a patient using a perfusion catheter assembly having an introducer catheter, perfusion catheter tip and a guide wire, comprising:

a. inserting the introducer catheter percutaneously in a femoral artery of the patient;
   b. maneuvering a distal end of the introducer catheter to a position in the aorta that is adjacent to an inlet to a renal artery;
   c. at least partially blocking the inlet to the renal artery by abutting a distal end of the introducer catheter against the inlet while the distal end of the introducer catheter remains entirely in the aorta, wherein said distal end of the introducer catheter includes a sealing device sufficiently large to substantially seal the inlet to the renal artery and sufficiently small to avoid substantially disrupting blood flow through the aorta;
   d. positioning the perfusion catheter tip through a distal portion of the introducer catheter, and into the renal artery, wherein an inlet to the catheter tip is proximate to the distal portion of the introducer catheter;
   e. attaching a proximate portion of the perfusion catheter assembly to a perfusate supply, and
   f. pumping perfusate from the perfusate supply through the introducer catheter into the inlet to the catheter tip through the perfusion catheter tip, and into the renal artery to perfuse the kidney.

10. A method as in claim 9 further including steps (g) of monitoring pressure in the renal artery and (h) controlling blood flow through the introducer catheter and the perfusion catheter tip to sustain a predetermined pressure in the renal artery.

11. A method of perfusion of a kidney in a patient having a beating heart, using a perfusion catheter assembly having an introducer catheter and a perfusion catheter tip extending from a distal end of the introducer catheter, wherein said introducer catheter includes a sealing balloon, said method comprising:

a. inserting the introducer catheter into an artery of the patient, maneuvering the perfusion catheter through an aorta and towards an inlet to a renal artery of the kidney;
   b. positioning the distal end of the introducer catheter in the aorta proximate to an inlet to the renal artery;
   c. inserting the perfusion catheter tip extending from the introducer catheter into the renal artery, wherein said catheter tip has an inlet proximate a distal end of the introducer catheter;
   d. delivering perfusate though the introducer catheter, into the inlet of the catheter tip, through the perfusion catheter tip and into the renal artery to perfuse the kidney;
   e. positioning the sealing balloon entirely in the aorta and against the inlet to the renal artery, and
   f. inflating the sealing balloon in the aorta to cover the entrance into the renal artery and block retrograde flow from the renal artery into the aorta, wherein said inflated sealing balloon is sufficiently large to substantially seal the inlet to the renal artery and sufficiently small to avoid substantially disrupting blood flow through the aorta.

* * * * *